United States Patent
Johnson

(10) Patent No.: US 9,282,259 B2
(45) Date of Patent: Mar. 8, 2016

(54) CAMERA AND METHOD FOR THERMAL IMAGE NOISE REDUCTION USING POST PROCESSING TECHNIQUES

(71) Applicant: Fluke Corporation, Everett, WA (US)

(72) Inventor: Kirk R. Johnson, Rogers, MN (US)

(73) Assignee: Fluke Corporation, Everett, WA (US)

( * ) Notice: Subject to any disclaimer, the term of this patent is extended or adjusted under 35 U.S.C. 154(b) by 568 days.

(21) Appl. No.: 13/709,352

(22) Filed: Dec. 10, 2012

(65) Prior Publication Data

US 2014/0160298 A1  Jun. 12, 2014

(51) Int. Cl.
*H04N 5/33* (2006.01)
*H04N 5/232* (2006.01)
*H04N 5/235* (2006.01)

(52) U.S. Cl.
CPC ............... *H04N 5/33* (2013.01); *H04N 5/2355* (2013.01); *H04N 5/23254* (2013.01); *H04N 5/23274* (2013.01); *H04N 5/23277* (2013.01); *H04N 5/332* (2013.01)

(58) Field of Classification Search
USPC ...................................... 348/222.1, 164–168
See application file for complete search history.

(56) References Cited

U.S. PATENT DOCUMENTS

| | | | |
|---|---|---|---|
| 4,593,311 A | 6/1986 | Levine | |
| 6,630,950 B1 | 10/2003 | Ohkawara | |
| 6,778,210 B1 | 8/2004 | Sugahara | |
| 7,705,884 B2 | 4/2010 | Pinto et al. | |
| 7,755,667 B2 | 7/2010 | Rabbani | |
| 7,782,362 B2 | 8/2010 | Oshima | |
| 7,783,128 B2 | 8/2010 | Kurata et al. | |
| 7,924,312 B2 | 4/2011 | Packard | |
| 8,306,275 B2 | 11/2012 | Hogasten | |
| 8,503,821 B2 | 8/2013 | Hogasten | |
| 8,525,904 B2 | 9/2013 | Mitsuya et al. | |
| 2002/0159651 A1 | 10/2002 | Tener | |
| 2005/0168583 A1 | 8/2005 | Thomason | |
| 2007/0247517 A1 | 10/2007 | Zhang et al. | |
| 2007/0296838 A1* | 12/2007 | Erdtmann | 348/243 |
| 2009/0230293 A1 | 9/2009 | Hogasten | |

(Continued)

FOREIGN PATENT DOCUMENTS

| | | |
|---|---|---|
| EP | 2453407 A1 | 5/2012 |
| GB | 2430573 A | 3/2007 |

(Continued)

OTHER PUBLICATIONS

Soonmin Bae, "Computational Re-Photography", (ACM Transactions in Graphics, vol. 29, No. 3, Article 24, Publication Date: Jun. 2010) 15 pages.

(Continued)

*Primary Examiner* — Nigar Chowdhury
(74) *Attorney, Agent, or Firm* — Fredrikson & Byron, P.A.

(57) ABSTRACT

Devices and methods for generating infrared (IR) images with improved quality are disclosed. In embodiments of the invention, temporal averaging techniques are used to reduce temporal noise that may be present in thermal images. This is especially useful in low-contrast thermal scenes, where a relatively small amount of thermal noise may become exceedingly prevalent. In order to average properly, some embodiments of the invention provide methods or means for aligning multiple images that are to be averaged together to eliminate inaccuracies and misrepresentations that may result from averaging misaligned images.

23 Claims, 11 Drawing Sheets

(56) References Cited

U.S. PATENT DOCUMENTS

| | | |
|---|---|---|
| 2009/0284609 A1 | 11/2009 | Matsunaga |
| 2010/0079606 A1 | 4/2010 | Batur |
| 2010/0134640 A1 | 6/2010 | Kuo et al. |
| 2010/0201828 A1 | 8/2010 | Mitsuya |
| 2013/0028477 A1 | 1/2013 | Schmieder et al. |
| 2013/0169819 A1 | 7/2013 | Strandemar |
| 2013/0321638 A1 | 12/2013 | Stratmann et al. |
| 2014/0015921 A1 | 1/2014 | Foi |
| 2014/0247365 A1 | 9/2014 | Gardner et al. |
| 2014/0363099 A1 | 12/2014 | Evers-Senne et al. |

FOREIGN PATENT DOCUMENTS

| | | |
|---|---|---|
| WO | WO2006/036398 A2 | 4/2006 |
| WO | WO2006/051525 A1 | 5/2006 |
| WO | WO2008/031089 A2 | 3/2008 |

OTHER PUBLICATIONS

Extended European Search Report for EP Application No. 13196324.1, dated Nov. 5, 2014, 5 pages.

\* cited by examiner

| | | | | |
|---|---|---|---|---|
| 24 | 19 | 14 | 9 | 4 |
| 23 | 18 | 13 | 8 | 3 |
| 22 | 17 | 12 | 7 | 2 |
| 21 | 16 | 11 | 6 | 1 |
| 20 | 15 | 10 | 5 | 0 |

FIG. 4b

| | | | | |
|---|---|---|---|---|
| (4,4) | (4,3) | (4,2) | (4,1) | (4,0) |
| (3,4) | (3,3) | (3,2) | (3,1) | (3,0) |
| (2,4) | (2,3) | (2,2) | (2,1) | (2,0) |
| (1,4) | (1,3) | (1,2) | (1,1) | (1,0) |
| (0,4) | (0,3) | (0,2) | (0,1) | (0,0) |

FIG. 4a

CAMERA AND METHOD FOR THERMAL IMAGE NOISE REDUCTION USING POST PROCESSING TECHNIQUES

BACKGROUND

Thermal imaging cameras are used in a variety of situations. For example, thermal imaging cameras are often used during maintenance inspections to thermally inspect equipment. Example equipment may include rotating machinery, electrical panels, or rows of circuit breakers, among other types of equipment. Thermal inspections can detect equipment hot spots such as overheating machinery or electrical components, helping to ensure timely repair or replacement of the overheating equipment before a more significant problem develops.

Depending on the configuration of the camera, the thermal imaging camera may also generate a visible light image of the same object. The camera may display the infrared image and the visible light image in a coordinated manner, for example, to help an operator interpret the thermal image generated by the thermal imaging camera. Unlike visible light images which generally provide good contrast between different objects, it is often difficult to recognize and distinguish different features in a thermal image as compared to the real-world scene.

Thermal noise, especially in low contrast thermal images, may pose additional problems when attempting to distinguish features within the images. Noise comparable with the temperature differences across an image may significantly alter the appearance of an image, making distinguishing between features even more difficult. While image averaging techniques have been used in the past to attempt to eliminate some of this random noise, these techniques have created additional image issues such as blurred edges and ghosting effects.

SUMMARY

In general, this disclosure is directed to a thermal imaging camera and method for providing thermal images wherein random noise is reduced through an averaging technique designed to reduce the negative byproducts of existing technology.

Various methods and devices fall within the scope of the present invention. Certain embodiments of the invention comprise a thermal imaging camera with at least one infrared (IR) sensor comprising a plurality of pixels. In some embodiments, each pixel may have a unique coordinate location. Certain cameras further comprise a display adapted to display at least a portion of an IR image detected from a target scene. In some embodiments of the invention, a thermal imaging camera comprises a processor that is programmed to capture a plurality of IR frames of a target scene. In certain embodiments, the processor further comprises instructions to average the plurality of frames in order to improve the overall image quality.

It may be that within the plurality of frames, a substantially fixed feature within the scene will be shifted in pixel coordinates from frame to frame. Accordingly, in certain embodiments of the invention a processor may be further programmed with steps to perform an alignment calculation in order to adjust the frames in such a way so that the substantially fixed feature is located in the same pixel coordinates amongst the plurality of frames. In yet further embodiments of the invention, the averaging performed by the processor is done on frames that have undergone such alignment calculation and adjustment.

Additional embodiments of the invention may further comprise a visible light (VL) sensor for detecting VL images of a target scene. A display may be configured to display at least a portion of this VL image and/or a portion of an alternatively or additionally captured IR image. In certain embodiments of the invention, a plurality of both VL and IR frames are captured by a thermal imaging camera. The IR frames may be averaged as described previously. In further embodiments, however, the IR frames may be aligned by means of an alignment calculation performed on the plurality of VL images.

Certain embodiments of the invention comprise a method for producing an IR image. In certain embodiments this image may comprise an average of a plurality of IR frames of a target scene. In further embodiments of the invention, an alignment calculation may be performed on the plurality of captured IR frames to adjust the frames in such that any substantially fixed feature within the plurality of frames is located in substantially the same pixel coordinates in each of the frames. In additional embodiments the plurality of frames are averaged after they are adjusted based on the alignment calculation.

The details of one or more examples are set forth in the accompanying drawings and the description below. Other features, objects, and advantages will be apparent from the description and drawings, and from the claims.

BRIEF DESCRIPTION OF DRAWINGS

FIGS. 4a and 4b are examples of pixel coordinate systems defined in an image.

DETAILED DESCRIPTION

The following detailed description is exemplary in nature and is not intended to limit the scope, applicability, or configuration of the invention in any way. Rather, the following description provides some practical illustrations for implementing various embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

A thermal imaging camera may be used to detect heat patterns across a scene, including an object or objects, under observation. The thermal imaging camera may detect infrared radiation given off by the scene and convert the infrared radiation into an infrared image indicative of the heat patterns. In some embodiments, the thermal imaging camera may also capture visible light from the scene and convert the visible light into a visible light image. Depending on the configuration of the thermal imaging camera, the camera may include infrared optics to focus the infrared radiation on an infrared sensor and visible light optics to focus the visible light on a visible light sensor.

Various embodiments provide methods and systems for producing thermal images with reduced noise using averaging techniques. To further improve image quality and eliminate problems that may arise from averaging (e.g. blurring, ghosting, etc.), an image alignment process is performed on the thermal images prior to averaging.

Figure 1:
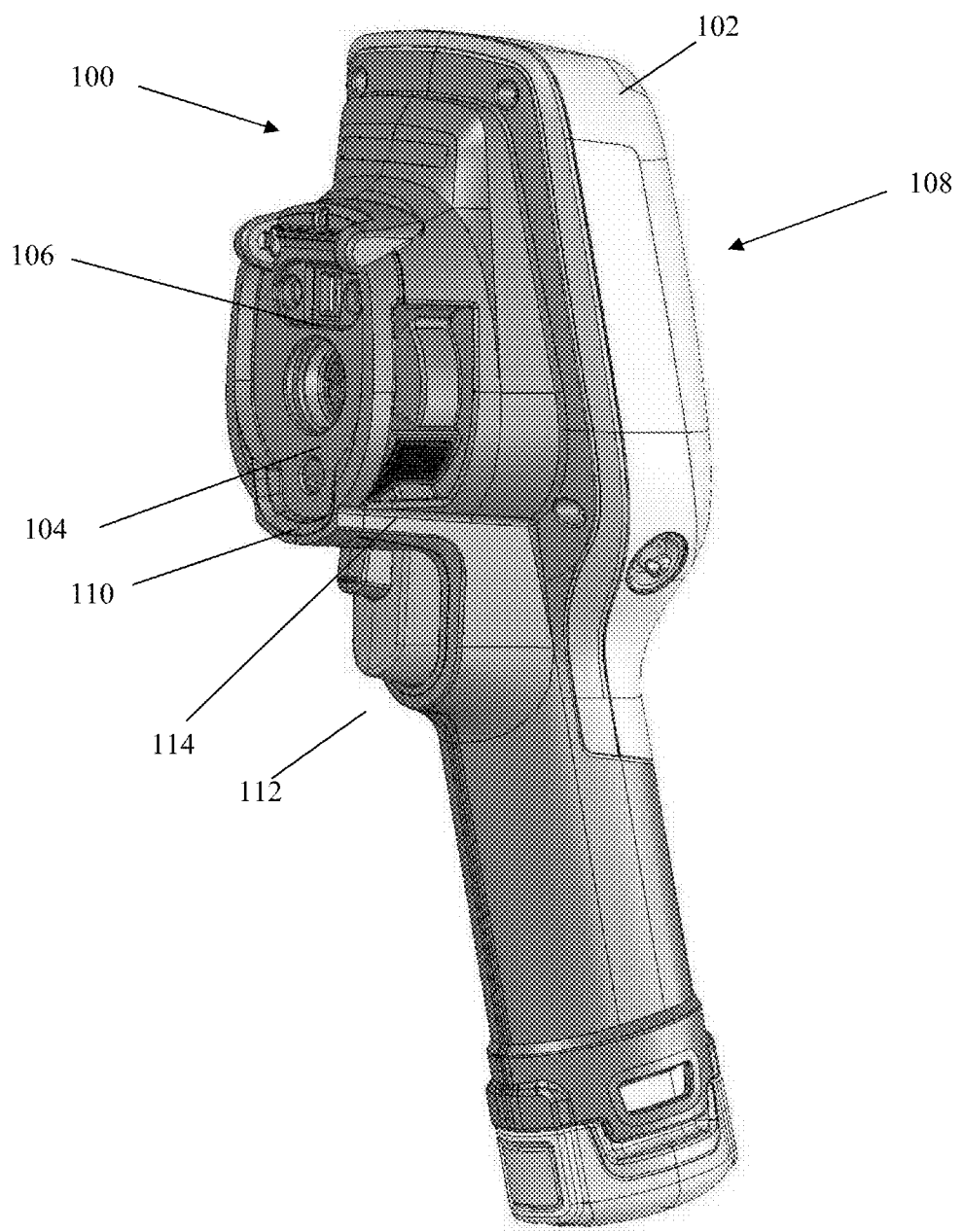
FIG. 1 is a perspective front view of a thermal imaging camera according to some embodiments.
Figure 2:
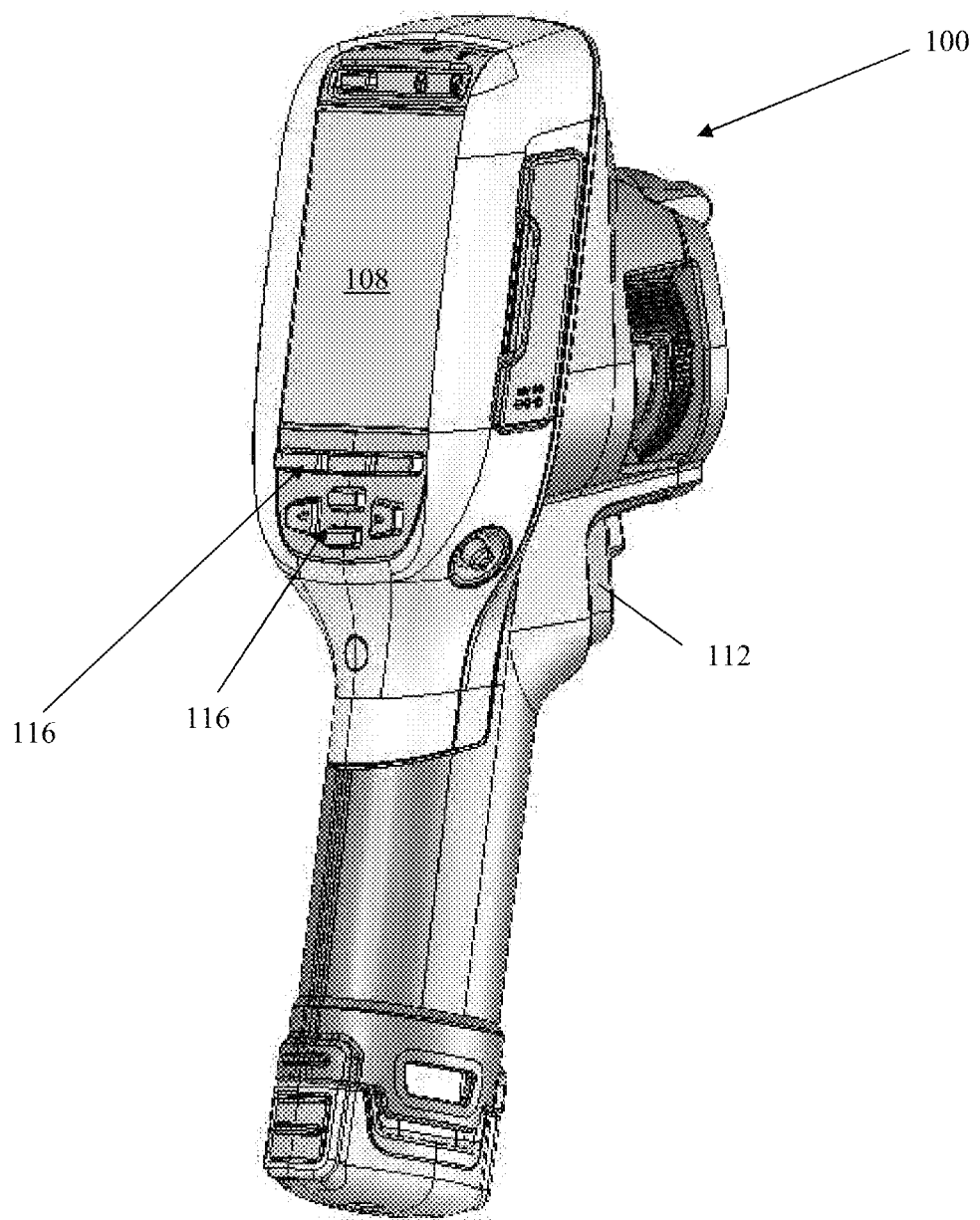
FIG. 2 is a perspective back view of the thermal imaging camera of FIG. 1.

FIGS. 1 and 2 show front and back perspective views, respectively of an example thermal imaging camera 100, which includes a housing 102, an infrared lens assembly 104, a visible light lens assembly 106, a display 108, a laser 110, and a trigger control 112. Housing 102 houses the various components of thermal imaging camera 100. The bottom portion of thermal imaging camera 100 includes a carrying handle for holding and operating the camera via one hand. Infrared lens assembly 104 receives infrared radiation from a scene and focuses the radiation on an infrared sensor for generating an infrared image of a scene. Visible light lens assembly 106 receives visible light from a scene and focuses the visible light on a visible light sensor for generating a visible light image of the same scene. Thermal imaging camera 100 captures the visible light image and/or the infrared image in response to depressing trigger control 112. In addition, thermal imaging camera 100 controls display 108 to display the infrared image and the visible light image generated by the camera, e.g., to help an operator thermally inspect a scene. Thermal imaging camera 100 may also include a focus mechanism coupled to infrared lens assembly 104 that is configured to move at least one lens of the infrared lens assembly so as to adjust the focus of an infrared image generated by the thermal imaging camera.

In operation, thermal imaging camera 100 detects heat patterns in a scene by receiving energy emitted in the infrared-wavelength spectrum from the scene and processing the infrared energy to generate a thermal image. Thermal imaging camera 100 may also generate a visible light image of the same scene by receiving energy in the visible light-wavelength spectrum and processing the visible light energy to generate a visible light image. As described in greater detail below, thermal imaging camera 100 may include an infrared camera module that is configured to capture an infrared image of the scene and a visible light camera module that is configured to capture a visible light image of the same scene. The infrared camera module may receive infrared radiation projected through infrared lens assembly 104 and generate therefrom infrared image data. The visible light camera module may receive light projected through visible light lens assembly 106 and generate therefrom visible light data.

In some examples, thermal imaging camera 100 collects or captures the infrared energy and visible light energy substantially simultaneously (e.g., at the same time) so that the visible light image and the infrared image generated by the camera are of the same scene at substantially the same time. In these examples, the infrared image generated by thermal imaging camera 100 is indicative of localized temperatures within the scene at a particular period of time while the visible light image generated by the camera is indicative of the same scene at the same period of time. In other examples, thermal imaging camera may capture infrared energy and visible light energy from a scene at different periods of time.

Visible light lens assembly 106 includes at least one lens that focuses visible light energy on a visible light sensor for generating a visible light image. Visible light lens assembly 106 defines a visible light optical axis which passes through the center of curvature of the at least one lens of the assembly. Visible light energy projects through a front of the lens and focuses on an opposite side of the lens. Visible light lens assembly 106 can include a single lens or a plurality of lenses (e.g., two, three, or more lenses) arranged in series. In addition, visible light lens assembly 106 can have a fixed focus or can include a focus adjustment mechanism for changing the focus of the visible light optics. In examples in which visible light lens assembly 106 includes a focus adjustment mechanism, the focus adjustment mechanism may be a manual adjustment mechanism or an automatic adjustment mechanism.

Infrared lens assembly 104 also includes at least one lens that focuses infrared energy on an infrared sensor for generating a thermal image. Infrared lens assembly 104 defines an infrared optical axis which passes through the center of curvature of lens of the assembly. During operation, infrared energy is directed through the front of the lens and focused on an opposite side of the lens. Infrared lens assembly 104 can include a single lens or a plurality of lenses (e.g., two, three, or more lenses), which may be arranged in series.

As briefly described above, thermal imaging camera 100 includes a focus mechanism for adjusting the focus of an infrared image captured by the camera. In the example shown in FIGS. 1 and 2, thermal imaging camera 100 includes focus ring 114. Focus ring 114 is operatively coupled (e.g., mechanically and/or electrically coupled) to at least one lens of infrared lens assembly 104 and configured to move the at least one lens to various focus positions so as to focus the infrared image captured by thermal imaging camera 100. Focus ring 114 may be manually rotated about at least a portion of housing 102 so as to move the at least one lens to which the focus ring is operatively coupled. In some examples, focus ring 114 is also operatively coupled to display 108 such that rotation of focus ring 114 causes at least a portion of a visible light image and at least a portion of an infrared image concurrently displayed on display 108 to move relative to one another. In different examples, thermal imaging camera 100 may include a manual focus adjustment mechanism that is implemented in a configuration other than focus ring 114, or may, in other embodiments, simply maintain a fixed focus.

In some examples, thermal imaging camera 100 may include an automatically adjusting focus mechanism in addition to or in lieu of a manually adjusting focus mechanism. An automatically adjusting focus mechanism may be operatively coupled to at least one lens of infrared lens assembly 104 and configured to automatically move the at least one lens to various focus positions, e.g., in response to instructions from thermal imaging camera 100. In one application of such an example, thermal imaging camera 100 may use laser 110 to electronically measure a distance between an object in a target scene and the camera, referred to as the distance-to-target. Thermal imaging camera 100 may then control the automatically adjusting focus mechanism to move the at least one lens of infrared lens assembly 104 to a focus position that corresponds to the distance-to-target data determined by thermal imaging camera 100. The focus position may correspond to the distance-to-target data in that the focus position may be configured to place the object in the target scene at the determined distance in focus. In some examples, the focus position set by the automatically adjusting focus mechanism may be manually overridden by an operator, e.g., by rotating focus ring 114.

Data of the distance-to-target, as measured by the laser 110, can be stored and associated with the corresponding captured image. For images which are captured using automatic focus, this data will be gathered as part of the focusing process. In some embodiments, the thermal imaging camera will also detect and save the distance-to-target data when an image is captured. This data may be obtained by the thermal imaging camera when the image is captured by using the laser 110 or, alternatively, by detecting the lens position and correlating the lens position to a known distance-to-target associated with that lens position. The distance-to-target data may be used by the thermal imaging camera 100 to direct the user to position the camera at the same distance from the target, such as by directing a user to move closer or further from the target based on laser measurements taken as the user repositions the camera, until the same distance-to-target is achieved as in an earlier image. The thermal imaging camera may further automatically set the lenses to the same positions as used in the earlier image, or may direct the user to reposition the lenses until the original lens settings are obtained.

During operation of thermal imaging camera 100, an operator may wish to view a thermal image of a scene and/or a visible light image of the same scene generated by the camera. For this reason, thermal imaging camera 100 may include a display. In the examples of FIGS. 1 and 2, thermal imaging camera 100 includes display 108, which is located on the back of housing 102 opposite infrared lens assembly 104 and visible light lens assembly 106. Display 108 may be configured to display a visible light image, an infrared image, and/or a combined image that is a simultaneous display of the visible light image and the infrared image. In different examples, display 108 may be remote (e.g., separate) from infrared lens assembly 104 and visible light lens assembly 106 of thermal imaging camera 100, or display 108 may be in a different spatial arrangement relative to infrared lens assembly 104 and/or visible light lens assembly 106. Therefore, although display 108 is shown behind infrared lens assembly 104 and visible light lens assembly 106 in FIG. 2, other locations for display 108 are possible.

Thermal imaging camera 100 can include a variety of user input media for controlling the operation of the camera and adjusting different settings of the camera. Example control functions may include adjusting the focus of the infrared and/or visible light optics, opening/closing a shutter, capturing an infrared and/or visible light image, or the like. In the example of FIGS. 1 and 2, thermal imaging camera 100 includes a depressible trigger control 112 for capturing an infrared and visible light image, and buttons 116, which form part of the user interface, for controlling other aspects of the operation of the camera. A different number or arrangement of user input media are possible, and it should be appreciated that the disclosure is not limited in this respect. For example, thermal imaging camera 100 may include a touch screen display 108 which receives user input by depressing different portions of the screen.

Figure 3:
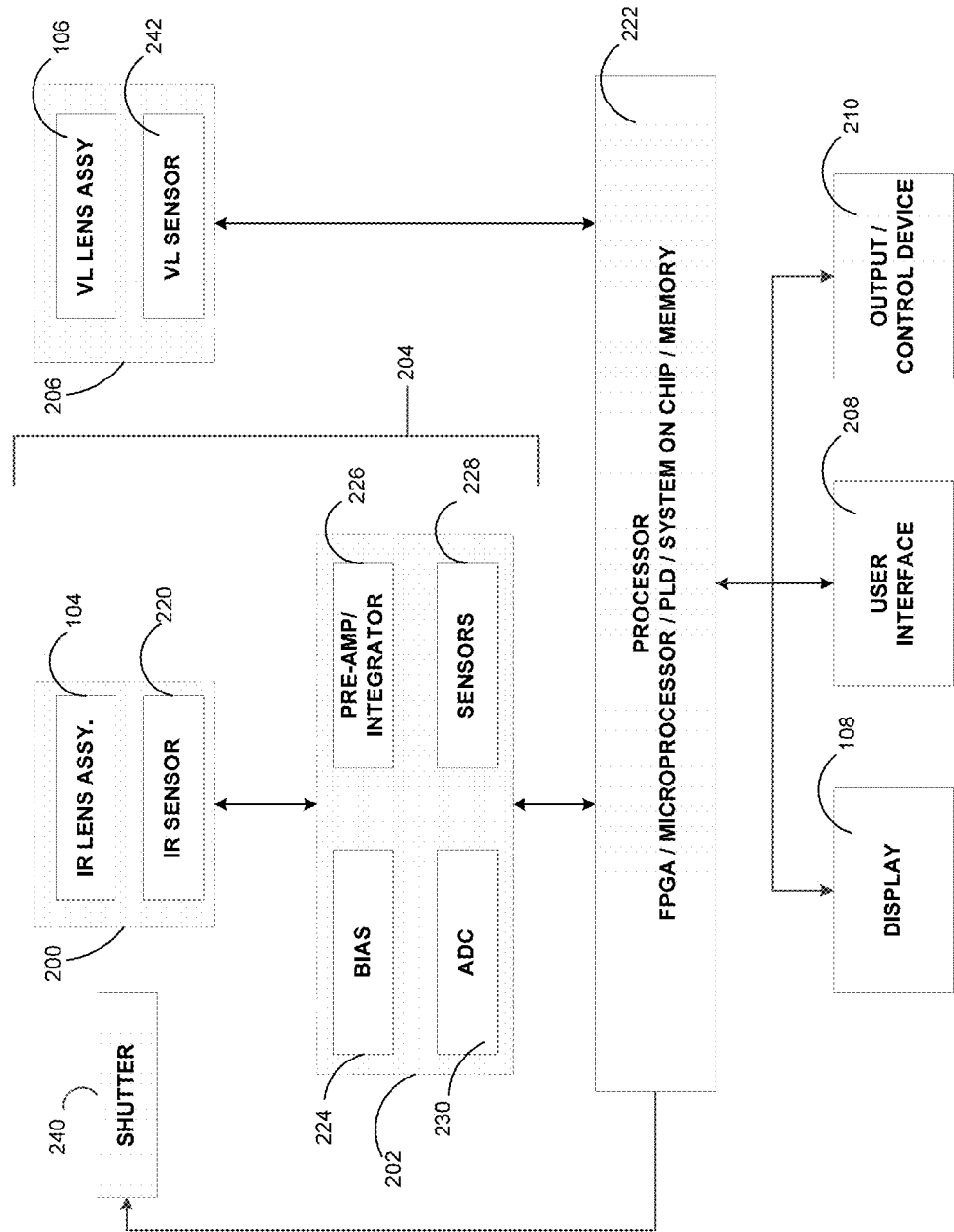
FIG. 3 is a functional block diagram illustrating components of thermal imaging cameras according to some embodiments.

FIG. 3 is a functional block diagram illustrating components of an example of thermal imaging camera 100. Thermal imaging camera 100 includes an IR camera module 200, front end circuitry 202. The IR camera module 200 and front end circuitry 202 are sometimes referred to in combination as front end stage or front end components 204 of the infrared camera 100. Thermal imaging camera 100 may also include a visible light camera module 206, a display 108, a user interface 208, and an output/control device 210.

Infrared camera module 200 may be configured to receive infrared energy emitted by a target scene and to focus the infrared energy on an infrared sensor for generation of infrared energy data, e.g., that can be displayed in the form of an infrared image on display 108 and/or stored in memory. Infrared camera module 200 can include any suitable components for performing the functions attributed to the module herein. In the example of FIG. 3, infrared camera module 200 is illustrated as including infrared lens assembly 104 and infrared sensor 220. As described above with respect to FIGS. 1 and 2, infrared lens assembly 104 includes at least one lens that takes infrared energy emitted by a target scene and focuses the infrared energy on infrared sensor 220. Infrared sensor 220 responds to the focused infrared energy by generating an electrical signal that can be converted and displayed as an infrared image on display 108.

Infrared lens assembly 104 can have a variety of different configurations. In some examples, infrared lens assembly 104 defines an F-number (which may also be referred to as a focal ratio or F-stop) of a specific magnitude. An approximate F-number may be determined by dividing the effective focal length of a lens assembly by a diameter of an entrance to the lens assembly (e.g., an outermost lens of infrared lens assembly 104), which may be indicative of the amount of infrared radiation entering the lens assembly. In general, increasing the F-number of infrared lens assembly 104 may increase the depth-of-field, or distance between nearest and farthest objects in a target scene that are in acceptable focus, of the lens assembly. An increased depth of field may help achieve acceptable focus when viewing different objects in a target scene with the infrared optics of thermal imaging camera 100 set at a hyperfocal position. If the F-number of infrared lens assembly 104 is increased too much, however, the diffraction effects will decrease spatial resolution (e.g., clarity) such that a target scene may not be in acceptable focus. An increased F-number may also reduce the thermal sensitivity (e.g., the noise-equivalent temperature difference will worsen).

Infrared sensor 220 may include one or more focal plane arrays (FPA) that generate electrical signals in response to infrared energy received through infrared lens assembly 104. Each FPA can include a plurality of infrared sensor elements including, e.g., bolometers, photon detectors, or other suitable infrared sensor elements. In operation, each sensor element, which may each be referred to as a sensor pixel, may change an electrical characteristic (e.g., voltage or resistance) in response to absorbing infrared energy received from a target scene. In turn, the change in electrical characteristic can provide an electrical signal that can be received by a processor 222 and processed into an infrared image displayed on display 108.

For instance, in examples in which infrared sensor 220 includes a plurality of bolometers, each bolometer may absorb infrared energy focused through infrared lens assembly 104 and increase in temperature in response to the absorbed energy. The electrical resistance of each bolometer may change as the temperature of the bolometer changes. With each detector element functioning as a pixel, a two-dimensional image or picture representation of the infrared radiation can be further generated by translating the changes in resistance of each detector element into a time-multiplexed electrical signal that can be processed for visualization on a display or storage in memory (e.g., of a computer). Processor 222 may measure the change in resistance of each bolometer by applying a current (or voltage) to each bolometer and measure the resulting voltage (or current) across the bolometer. Based on these data, processor 222 can determine the amount of infrared energy emitted by different portions of a target scene and control display 108 to display a thermal image of the target scene.

Independent of the specific type of infrared sensor elements included in the FPA of infrared sensor 220, the FPA array can define any suitable size and shape. In some examples, infrared sensor 220 includes a plurality of infrared sensor elements arranged in a grid pattern such as, e.g., an array of sensor elements arranged in vertical columns and horizontal rows. In various examples, infrared sensor 220 may include an array of vertical columns by horizontal rows of, e.g., 16×16, 50×50, 160×120, 120×160 or 650×480. In other examples, infrared sensor 220 may include a smaller number of vertical columns and horizontal rows (e.g., 1×1), a larger number vertical columns and horizontal rows (e.g., 1000×1000), or a different ratio of columns to rows.

In certain embodiments a Read Out Integrated Circuit (ROIC) is incorporated on the IR sensor 220. The ROIC is used to output signals corresponding to each of the pixels. Such ROIC is commonly fabricated as an integrated circuit on a silicon substrate. The plurality of detector elements may be fabricated on top of the ROIC, wherein their combination provides for the IR sensor 220. In some embodiments, the ROIC can include components discussed elsewhere in this disclosure (e.g. an analog-to-digital converter (ADC)) incorporated directly onto the FPA circuitry. Such integration of the ROIC, or other further levels of integration not explicitly discussed, should be considered within the scope of this disclosure.

As described above, the IR sensor 220 generates a series of electrical signals corresponding to the infrared radiation received by each infrared detector element to represent a thermal image. A "frame" of thermal image data is generated when the voltage signal from each infrared detector element is obtained by scanning all of the rows that make up the IR sensor 220. Again, in certain embodiments involving bolometers as the infrared detector elements, such scanning is done by switching a corresponding detector element into the system circuit and applying a bias voltage across such switched-in element. Successive frames of thermal image data are generated by repeatedly scanning the rows of the IR sensor 220, with such frames being produced at a rate sufficient to generate a video representation (e.g. 30 Hz, or 60 Hz) of the thermal image data.

The front end circuitry 202 includes circuitry for interfacing with and controlling the IR camera module 200. In addition, the front end circuitry 202 initially processes and transmits collected infrared image data to a processor 222 via a connection therebetween. More specifically, the signals generated by the IR sensor 220 are initially conditioned by the front end circuitry 202 of the thermal imaging camera 100. In certain embodiments, as shown, the front end circuitry 202 includes a bias generator 224 and a pre-amp/integrator 226. In addition to providing the detector bias, the bias generator 224 can optionally add or subtract an average bias current from the total current generated for each switched-in detector element. The average bias current can be changed in order (i) to compensate for deviations to the entire array of resistances of the detector elements resulting from changes in ambient temperatures inside the thermal imaging camera 100 and (ii) to compensate for array-to-array variations in the average detector elements of the IR sensor 220. Such bias compensation can be automatically controlled by the thermal imaging camera 100 or software, or can be user controlled via input to the output/control device 210 or processor 222. Following provision of the detector bias and optional subtraction or addition of the average bias current, the signals can be passed through a pre-amp/integrator 226. Typically, the pre-amp/integrator 226 is used to condition incoming signals, e.g., prior to their digitization. As a result, the incoming signals can be adjusted to a form that enables more effective interpretation of the signals, and in turn, can lead to more effective resolution of the created image. Subsequently, the conditioned signals are sent downstream into the processor 222 of the thermal imaging camera 100.

In some embodiments, the front end circuitry 202 can include one or more additional elements for example, additional sensors 228 or an ADC 230. Additional sensors 228 can include, for example, temperature sensors, visual light sensors (such as a CCD), pressure sensors, magnetic sensors, etc. Such sensors can provide additional calibration and detection information to enhance the functionality of the thermal imaging camera 100. For example, temperature sensors can provide an ambient temperature reading near the IR sensor 220 to assist in radiometry calculations. A magnetic sensor, such as a Hall effect sensor, can be used in combination with a magnet mounted on the lens to provide lens focus position information. Such information can be useful for calculating distances, or determining a parallax offset for use with visual light scene data gathered from a visual light sensor.

An ADC 230 can provide the same function and operate in substantially the same manner as discussed below, however its inclusion in the front end circuitry 202 may provide certain benefits, for example, digitization of scene and other sensor information prior to transmittal to the processor 222 via the connection therebetween. In some embodiments, the ADC 230 can be integrated into the ROIC, as discussed above, thereby eliminating the need for a separately mounted and installed ADC 230.

In some embodiments, front end components can further include a shutter 240. A shutter 240 can be externally or internally located relative to the lens and operate to open or close the view provided by the IR lens assembly 104. As is known in the art, the shutter 240 can be mechanically positionable, or can be actuated by an electro-mechanical device such as a DC motor or solenoid. Embodiments of the invention may include a calibration or setup software implemented method or setting which utilize the shutter 240 to establish appropriate bias levels for each detector element.

Components described as processors within thermal imaging camera 100, including processor 222, may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. Processor 222 may also include memory that stores program instructions and related data that, when executed by processor 222, cause thermal imaging camera 100 and processor 222 to perform the functions attributed to them in this disclosure. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A removable memory may also allow image data to be easily transferred to another computing device, or to be removed before thermal imaging camera 100 is used in another application. Processor 222 may also be implemented as a System on Chip that integrates all components of a computer or other electronic system into a single chip. These elements manipulate the conditioned scene image data delivered from the front end stages 204 in order to provide output scene data that can be displayed or stored for use by the user. Subsequently, the processor 222 (processing circuitry) sends the processed data to a display 108 or other output/control device 210.

During operation of thermal imaging camera 100, processor 222 can control infrared camera module 200 to generate infrared image data for creating an infrared image. Processor 222 can generate a digital "frame" of infrared image data. By generating a frame of infrared image data, processor 222 captures an infrared image of a target scene at a given point in time.

Processor 222 can capture a single infrared image or "snap shot" of a target scene by measuring the electrical signal of each infrared sensor element included in the FPA of infrared sensor 220 a single time. Alternatively, processor 222 can capture a plurality of infrared images of a target scene by repeatedly measuring the electrical signal of each infrared sensor element included in the FPA of infrared sensor 220. In examples in which processor 222 repeatedly measures the electrical signal of each infrared sensor element included in the FPA of infrared sensor 220, processor 222 may generate a dynamic thermal image (e.g., a video representation) of a target scene. For example, processor 222 may measure the electrical signal of each infrared sensor element included in the FPA at a rate sufficient to generate a video representation of thermal image data such as, e.g., 30 Hz or 60 Hz. Processor 222 may perform other operations in capturing an infrared image such as sequentially actuating a shutter 240 to open and close an aperture of infrared lens assembly 104, or the like.

With each sensor element of infrared sensor 220 functioning as a sensor pixel, processor 222 can generate a two-dimensional image or picture representation of the infrared radiation from a target scene by translating changes in an electrical characteristic (e.g., resistance) of each sensor element into a time-multiplexed electrical signal that can be processed, e.g., for visualization on display 108 and/or storage in memory. Processor 222 may perform computations to convert raw infrared image data into scene temperatures (radiometry) including, in some examples, colors corresponding to the scene temperatures.

Processor 222 may control display 108 to display at least a portion of an infrared image of a captured target scene. In some examples, processor 222 controls display 108 so that the electrical response of each sensor element of infrared sensor 220 is associated with a single pixel on display 108. In other examples, processor 222 may increase or decrease the resolution of an infrared image so that there are more or fewer pixels displayed on display 108 than there are sensor elements in infrared sensor 220. Processor 222 may control display 108 to display an entire infrared image (e.g., all portions of a target scene captured by thermal imaging camera 100) or less than an entire infrared image (e.g., a lesser port of the entire target scene captured by thermal imaging camera 100). Processor 222 may perform other image processing functions, as described in greater detail below.

Independent of the specific circuitry, thermal imaging camera 100 may be configured to manipulate data representative of a target scene so as to provide an output that can be displayed, stored, transmitted, or otherwise utilized by a user.

Thermal imaging camera 100 includes visible light camera module 206. Visible light camera module 206 may be configured to receive visible light energy from a target scene and to focus the visible light energy on a visible light sensor for generation of visible light energy data, e.g., that can be displayed in the form of a visible light image on display 108 and/or stored in memory. Visible light camera module 206 can include any suitable components for performing the functions attributed to the module herein. In the example of FIG. 3, visible light camera module 206 is illustrated as including visible light lens assembly 106 and visible light sensor 242. As described above with respect to FIGS. 1 and 2, visible light lens assembly 106 includes at least one lens that takes visible light energy emitted by a target scene and focuses the visible light energy on visible light sensor 242. Visible light sensor 242 responds to the focused energy by generating an electrical signal that can be converted and displayed as a visible light image on display 108.

Visible light sensor 242 may include a plurality of visible light sensor elements such as, e.g., CMOS detectors, CCD detectors, PIN diodes, avalanche photo diodes, or the like. The number of visible light sensor elements may be the same as or different than the number of infrared light sensor elements.

In operation, optical energy received from a target scene may pass through visible light lens assembly 106 and be focused on visible light sensor 242. When the optical energy impinges upon the visible light sensor elements of visible light sensor 242, photons within the photodetectors may be released and converted into a detection current. Processor 222 can process this detection current to form a visible light image of the target scene.

During use of thermal imaging camera 100, processor 222 can control visible light camera module 206 to generate visible light data from a captured target scene for creating a visible light image. The visible light data may include luminosity data indicative of the color(s) associated with different portions of the captured target scene and/or the magnitude of light associated with different portions of the captured target scene. Processor 222 can generate a "frame" of visible light image data by measuring the response of each visible light sensor element of thermal imaging camera 100 a single time. By generating a frame of visible light data, processor 222 captures visible light image of a target scene at a given point in time. Processor 222 may also repeatedly measure the response of each visible light sensor element of thermal imaging camera 100 so as to generate a dynamic thermal image (e.g., a video representation) of a target scene, as described above with respect to infrared camera module 200.

With each sensor element of visible light camera module 206 functioning as a sensor pixel, processor 222 can generate a two-dimensional image or picture representation of the visible light from a target scene by translating an electrical response of each sensor element into a time-multiplexed electrical signal that can be processed, e.g., for visualization on display 108 and/or storage in memory.

Processor 222 may control display 108 to display at least a portion of a visible light image of a captured target scene. In some examples, processor 222 controls display 108 so that the electrical response of each sensor element of visible light camera module 206 is associated with a single pixel on display 108. In other examples, processor 222 may increase or decrease the resolution of a visible light image so that there are more or fewer pixels displayed on display 108 than there are sensor elements in visible light camera module 206. Processor 222 may control display 108 to display an entire visible light image (e.g., all portions of a target scene captured by thermal imaging camera 100) or less than an entire visible light image (e.g., a lesser port of the entire target scene captured by thermal imaging camera 100).

As noted above, processor 222 may be configured to determine a distance between thermal imaging camera 100 and an object in a target scene captured by a visible light image and/or infrared image generated by the camera. Processor 222 may determine the distance based on a focus position of the infrared optics associated with the camera. For example, processor 222 may detect a position (e.g., a physical position) of a focus mechanism associated with the infrared optics of the camera (e.g., a focus position associated with the infrared optics) and determine a distance-to-target value associated with the position. Processor 222 may then reference data stored in memory that associates different positions with different distance-to-target values to determine a specific distance between thermal imaging camera 100 and the object in the target scene.

In these and other examples, processor 222 may control display 108 to concurrently display at least a portion of the visible light image captured by thermal imaging camera 100 and at least a portion of the infrared image captured by thermal imaging camera 100. Such a concurrent display may be useful in that an operator may reference the features displayed in the visible light image to help understand the features concurrently displayed in the infrared image, as the operator may more easily recognize and distinguish different real-world features in the visible light image than the infrared image. In various examples, processor 222 may control display 108 to display the visible light image and the infrared image in side-by-side arrangement, in a picture-in-picture arrangement, where one of the images surrounds the other of the images, or any other suitable arrangement where the visible light and the infrared image are concurrently displayed.

For example, processor 222 may control display 108 to display the visible light image and the infrared image in a combined arrangement. In a combined arrangement, the visible light image and the infrared image may be superimposed on top of one another. An operator may interact with user interface 208 to control the transparency or opaqueness of one or both of the images displayed on display 108. For example, the operator may interact with user interface 208 to adjust the infrared image between being completely transparent and completely opaque and also adjust the visible light image between being completely transparent and completely opaque. Such an example combined arrangement, which may be referred to as an alpha-blended arrangement, may allow an operator to adjust display 108 to display an infrared-only image, a visible light-only image, of any overlapping combination of the two images between the extremes of an infrared-only image and a visible light-only image. Processor 222 may also combined scene information with other data, such as radiometric data, alarm data, and the like.

Additionally, in some embodiments, the processor 222 can interpret and execute commands from user interface 208, an output/control device 210. This can involve processing of various input signals and transferring those signals to the front end circuitry 202 via a connection therebetween. Components (e.g. motors, or solenoids) proximate the front end circuitry 202 can be actuated to accomplish the desired control function. Exemplary control functions can include adjusting the focus, opening/closing a shutter, triggering sensor readings, adjusting bias values, etc. Moreover, input signals may be used to alter the processing of the image data that occurs in the processor 222.

Processor can further include other components to assist with the processing and control of the infrared imaging camera 100. For example, as discussed above, in some embodiments, an ADC can be incorporated into the processor 222. In such a case, analog signals conditioned by the front-end stages 204 are not digitized until reaching the processor 222. Moreover, some embodiments can include additional on board memory for storage of processing command information and scene data, prior to transmission to the display 108 or the output/control device 210.

An operator may interact with thermal imaging camera 100 via user interface 208, which may include buttons, keys, or another mechanism for receiving input from a user. The operator may receive output from thermal imaging camera 100 via display 108. Display 108 may be configured to display an infrared-image and/or a visible light image in any acceptable palette, or color scheme, and the palette may vary, e.g., in response to user control. In some examples, display 108 is configured to display an infrared image in a monochromatic palette such as grayscale or amber. In other examples, display 108 is configured to display an infrared image in a color palette such as, e.g., ironbow, blue-red, or other high contrast color scheme. Combination of grayscale and color palette displays are also contemplated.

While processor 222 can control display 108 to concurrently display at least a portion of an infrared image and at least a portion of a visible light image in any suitable arrangement, a picture-in-picture arrangement may help an operator to easily focus and/or interpret a thermal image by displaying a corresponding visible image of the same scene in adjacent alignment.

A power supply (not shown) delivers operating power to the various components of thermal imaging camera 100 and, in some examples, may include a rechargeable or non-rechargeable battery and a power generation circuit.

During operation of thermal imaging camera 100, processor 222 controls infrared camera module 200 and visible light camera module 206 with the aid of instructions associated with program information that is stored in memory to generate a visible light image and an infrared image of a target scene. Processor 222 further controls display 108 to display the visible light image and/or the infrared image generated by thermal imaging camera 100.

While post-processing and performing calculations on digital images, it is often convenient to assign coordinates to each pixel within said images. This allows for localization of features contained within the image, and a consistent means by which to reference various features within an image to one another or a particular location such as a the center or an edge of a frame. Implementing a coordinate system into a set of pixels may be done in several ways. FIGS. 4a and 4b exemplify two such ways, but it should be appreciated that methods are not limited to those disclosed herein.

FIG. 4a illustrates a two-dimensional pixel coordinate system. In this case, there are two axes representing a two-dimensional image, with each pixel being associated with a pair of coordinates, for example (1,1). Shifting one pixel to the right increases the first coordinate by one, while shifting to the left decreases the first coordinate by one. Similarly, shifting one pixel up increases the second coordinate by one, and shifting one pixel down decreases the second coordinate by one. In this particular example, the pixel in the bottom-left corner of the image is associated with coordinates (0,0). Accordingly, the pixel with coordinates (1,1) is one pixel above and one pixel to the right of the bottom-left corner.

FIG. 4b illustrates a pixel coordinate system wherein each pixel is assigned a single number. In this particular 25-pixel example, shifting one pixel to the right increases the coordinate by one, and shifting one pixel to the left decreases the coordinate by one, as was also the case in the previous example. However, in this arrangement, shifting one pixel up increases the coordinate by five and shifting one pixel down decreases the coordinate by five. In this example, the pixel in the bottom-left corner of the image is assigned location 0.

Accordingly, the coordinate one pixel above and one pixel to the right of pixel 0 is 0+1 (one pixel to the right)+5 (one pixel up)=6. More complicated arithmetic is necessary to find the location of a pixel given its coordinate in this arrangement, however.

Thermal scenes with low temperature contrast throughout can cause problems for thermal imaging cameras. If there is little temperature contrast (i.e., only small temperature differences) across an entire thermal scene, a small amount of noise in the data may obscure the actual temperature differences that are present. For example, if the camera has a noise equivalent temperature difference (NETD) of 50 mK (equivalently 0.050° C.), no two points within 0.050° C. from one another are readily distinguishable. Put another way, if, along with this NETD, the highest and lowest sensed temperatures are separated by 1° C. and the camera is displaying a range of 100 colors or shades to visually differentiate between temperatures, no five consecutive colors in this range can be differentiated with any reliability. This is because at any given point on the image, there could be up to 5 colors (or shades) of "noise" affecting the measurement and the display. This noise will obscure any temperature differences in the scene that are below the noise level.

Such noise may vary with time, being present at one point in one frame and gone or different the next. With this being the case, a temporal average of the data in multiple frames can serve to reduce this noise, thereby reducing the NETD and improving the signal to noise ratio. As more frames are taken into the average, the effective NETD of the scene decreases, increasing the thermal sensitivity of the device and the potential contrast of the scene. A thermal scene averaged from n individual frames decreases the NETD of the resulting image by a factor of $\sqrt{n}$.

Figure 5:
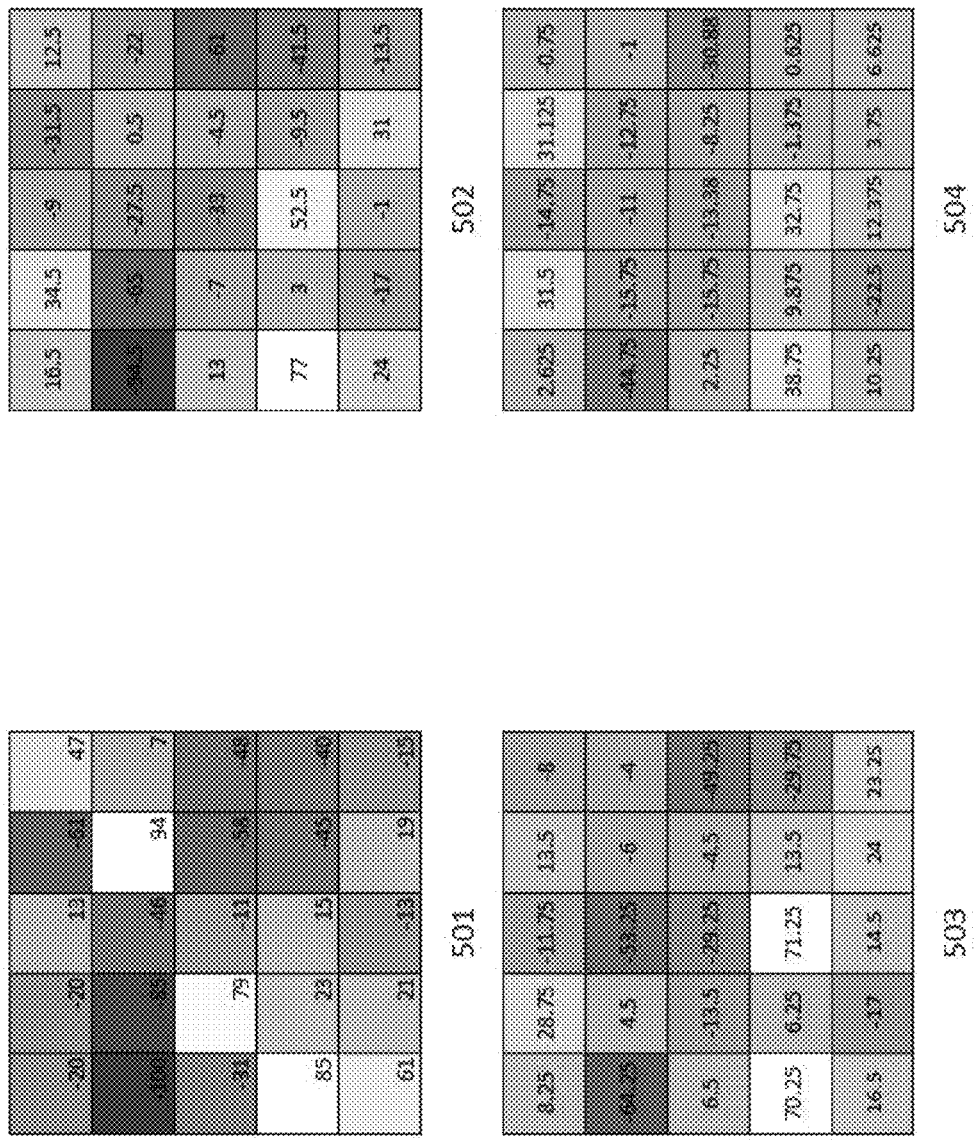
FIG. 5 shows a set of frames showing the effects of averaging on random noise.

FIG. 5 illustrates this reduction in noise with increased averaging. Shown are four representations of imaged noise (only data representing noise on each pixel is shown, no signal from thermal scene), shown as frame 501, frame 502, frame 503, and frame 504. Assuming the noise is completely random in time, eight five-pixel by five-pixel "images" (i.e. frames) were generated with pixels having a randomly populated number between −100 and 100 representing random amounts of thermal noise. Each image represents the same thermal image of a scene at a different point in time. Frame 501 represents the noise data from a single frame with no averaging, only random noise data. Frame 502 represents the average of two frames with random noise, reducing the NETD of the scene by a factor of $\sqrt{2}$. Frame 503 represents the average of four frames, reducing the NETD by a factor of 2 from the original scene. Frame 504 represents the average of eight random frames, again reducing the NETD, this time by a factor of $\sqrt{8}$ from the original frame. Each frame is color-coded to more clearly display differences in the noise signal—darker pixels represent lower values of noise. It is evident the wide range of noise present in frame 501 is greatly reduced via the averaging steps, as comparatively, frame 504 has very little contrast between pixels. This amounts to significantly reduced noise differences among pixels as the number of averaged frames increases, allowing for greater temperature resolution of a low-contrast thermal scene.

Certain embodiments of the invention employ an approach to averaging that entails capturing a plurality of scenes of an image, wherein each pixel of the scene has a value corresponding to the measured temperature associated with that pixel. Over the plurality of scenes, the values from the same pixel coordinates are averaged together, resulting in a calculated average value for each pixel. These averaged pixels are assembled together to construct an average image. Averaging, however, can be a source of additional error and/or undesirable image artifacts.

Figure 6:
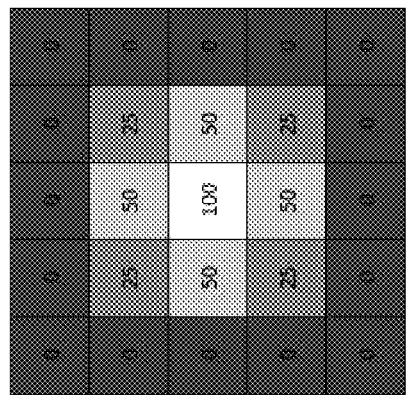
FIG. 6 illustrates the shortcomings of some averaging techniques by providing an example of an averaging calculation of four frames.
Figure 6:
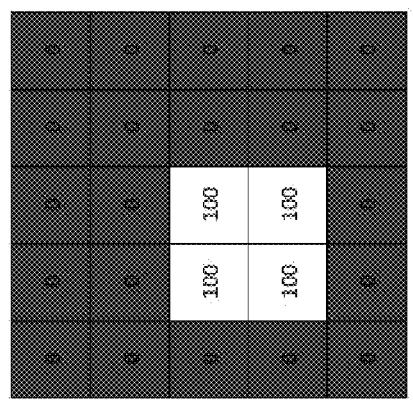
Figure 6:
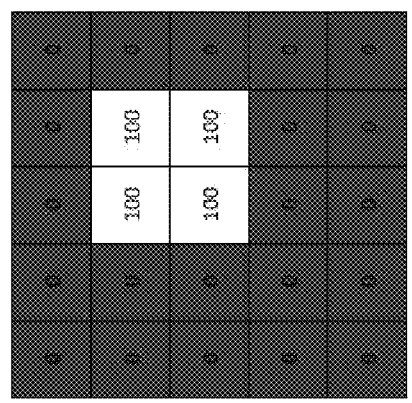
Figure 6:
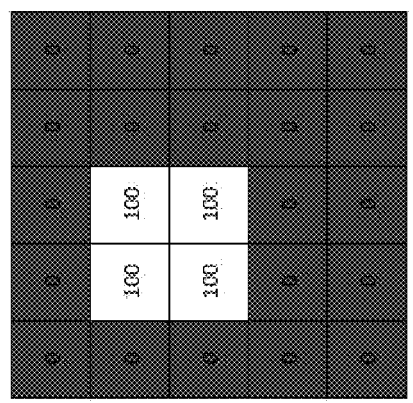
Figure 6:
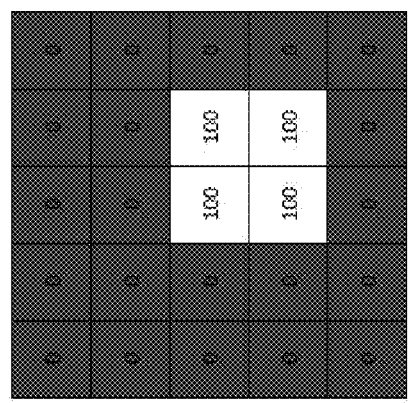

A common problem with averaging images is that the resulting image may contain blurred edges or ghosting artifacts due to misalignments of the frames being averaged. This is illustrated in FIG. 6, wherein a two pixel by two pixel square of uniform intensity representing a substantially fixed feature appears near the center of the frame in each of the four frames 601, 602, 603 and 604 that are to be averaged. The number in each square is meant as an exemplary value corresponding to a temperature associated with each pixel, while the shade of each square is meant to be a visual representation of the temperature associated with each pixel. The figure illustrates a situation in which, during the process of capturing of the four frames to be used, the location of the square object shifted in pixel coordinates, causing the resulting averaged image 605 to be a three pixel by three pixel square of varying intensity. This averaged image 605 is very different from any one of the individual frames, and therefore shows an inaccurate representation of the true scene. An alignment step in which like features are shifted to like coordinate locations prior to averaging will help fix this problem. One possible alignment step is outlined below.

If each frame is shifted with respect to its pixel coordinates by a proper amount, then the object in the image will be appropriately aligned in each frame prior to averaging, and this inaccuracy will not occur. For example, if using the two-dimensional coordinate system shown in FIG. 4a, the two-by-two box in each frame will have a definable location. In this case, the box comprises pixels:

(1,2), (2,2), (1,3), and (2,3) in frame one 601
(1,1), (2,1), (1,2), and (2,2) in frame two 602
(2,1), (3,1), (2,2), and (3,2) in frame three 603
(2,2), (3,2), (2,3), and (3,3) in frame four 604

After performing an alignment calculation, the imaging device decides how best to shift the pixel coordinates of the non-reference frames to most accurately align these frames with the reference frames. Examples of such calculations are known in the art, and may include a correlation or similar calculation. Additional alignment methods are disclosed in the paper entitled "Computational Re-Photography" by Bae et al. (ACM Transactions on Graphics, Vol. 29, No. 3, Article 24, Publication date: June 2010), as well as, by way of the transformation matrix, in the publication US2007/0247517 or by way of calculating a similarity figure as in U.S. Pat. No. 7,924,312, each of which are hereby incorporated by reference.

Figure 7:
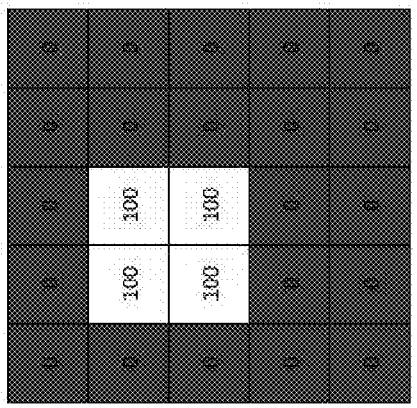
FIG. 7 illustrates the averaging of four frames with an additional correction made by an embodiment of the invention.
Figure 7:
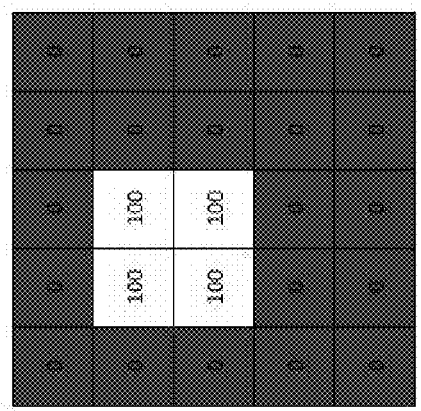
Figure 7:
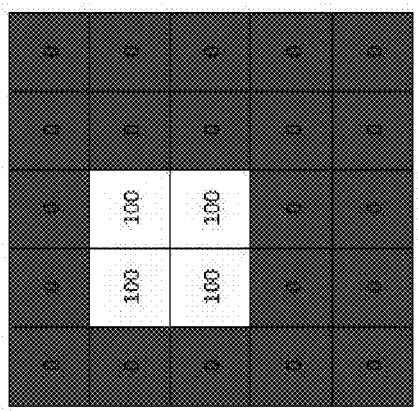
Figure 7:
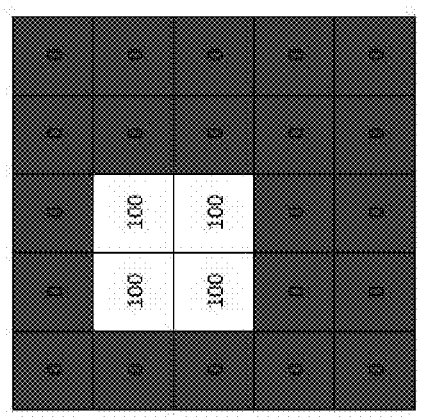
Figure 7:
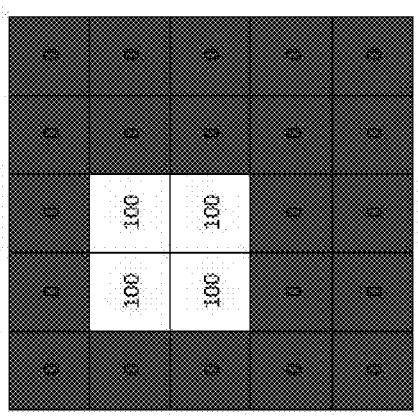

If, for example, the device chooses frame one 601 to be a reference frame, aligning the remaining frames with the reference frame requires the following coordinate shifts, calculated by subtracting the pixel location of a particular feature in one frame from the pixel location of the same feature in the reference frame. In this example, the feature used is the bottom-left corner of the imaged square:

frame one 601: no shift since it is the reference frame
frame two 602: (1,2)−(1,1)=(0,1); add (0,1) to all coordinates of frame two 602 prior to averaging
frame three 603: (1,2)−(2,1)=(−1,1); add (−1,1) to all coordinates of frame three 603 prior to averaging
frame four 604: (1,2)−(2,2)=(−1,0); (−1,0) to all coordinates of frame four 604 prior to averaging FIG. 7 shows the frames 701, 702, 703 and 704, representing the shifted result of the original frames 601, 602, 603 and 604 respectively. Averaged frame 705 shows the resulting image averaged from the shifted frames 701-704. As illustrated, performing these shifts prior to averaging the frames will cause the object, in this case the two-by-two square, to fall in the same pixel coordinate location in each of the frames 701, 702, 703 and 704, with a subsequent averaging calculation resulting in the averaged image 705—a more accurate representation of the original scene.

Figure 8:
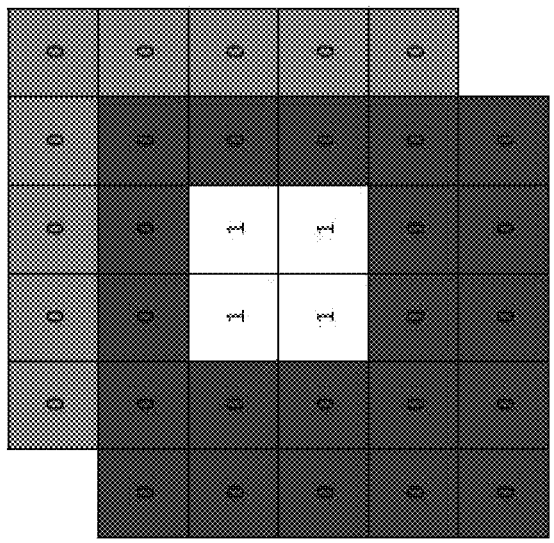
FIG. 8 the result of a correction and additional adjustment made by an embodiment of the invention.
Figure 8:
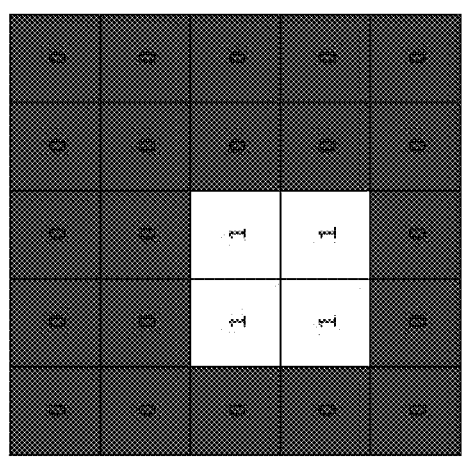
Figure 8:
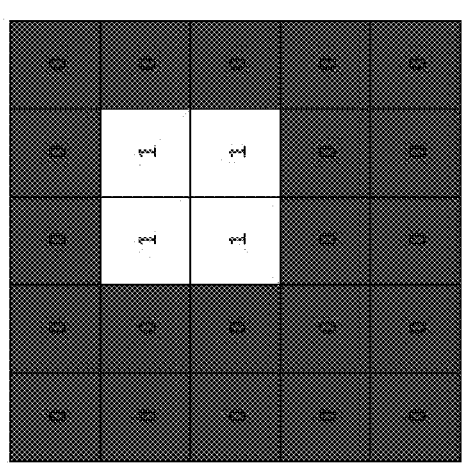
Figure 9A:
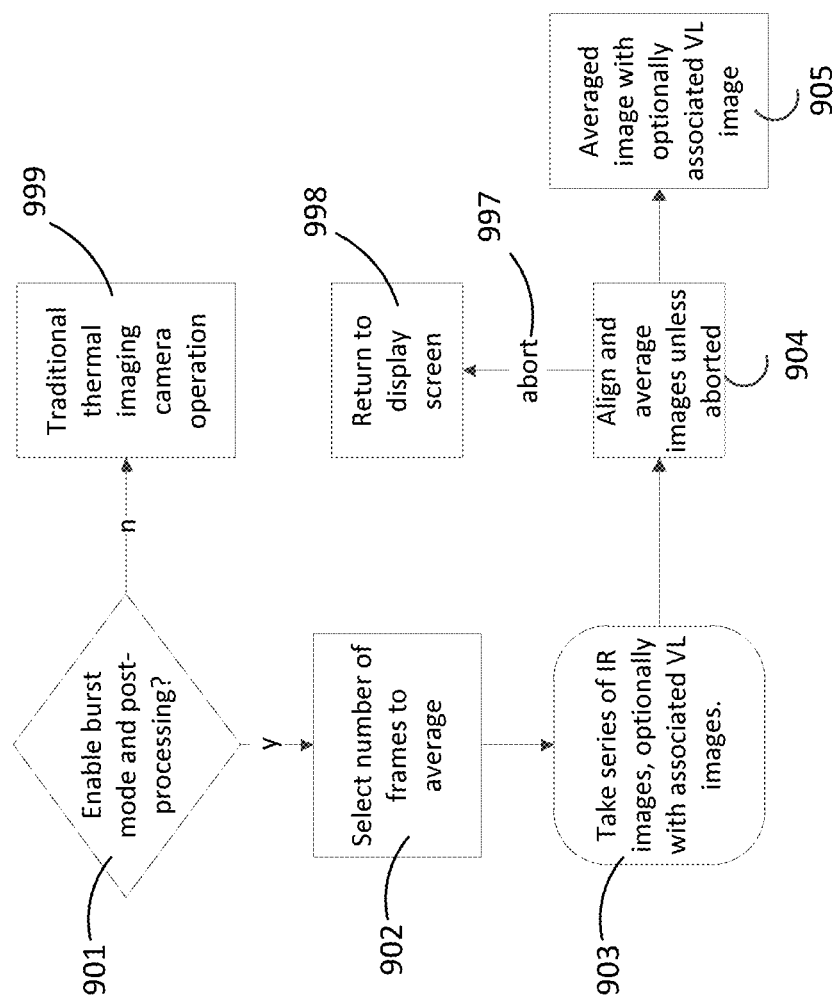
FIG. 9a is a process flow diagram outlining the basic operation of an embodiment of the invention.

If a frame is shifted to be aligned with a reference frame, the borders of the two frames will not coincide, and the frames will not entirely overlap. This will result in portions of the non-reference frames to be "hanging off" the edge of the reference frame after they have been shifted to align the elements of the scene. This is shown in FIG. 8, where a secondary frame 802 is shifted onto the reference frame 801 and the two are averaged. It can be seen, however, that there are "extra" pixels, shown here in a lighter grey, that do not fit into the reference frame. In certain embodiments of the invention, these pixels may simply be disregarded by the camera or somehow incorporated into the border of the image. In other embodiments, these "extra" pixels may be handled in other ways. FIG. 9*a* shows a flow diagram illustrating the general procedure of an embodiment of the invention as described thus far. A user chooses 901 to enable burst mode and post processing within the thermal imaging camera. If not enabled, the camera may operate as a traditional thermal imaging camera 999. If enabled, the user may select the number of frames to average 902 to form the resulting image. The selection may be made from a list, possibly comprising options of 2, 4, 8 . . . n images to be averaged together. In some embodiments, enabling of burst mode and the selection of the number of frames to average may be done via the user interface 116. In general, averaging more frames should be more effective at removing noise, but at the expense of processing time. In an alternative embodiment, the user may select the number of frames to average 902 prior to choosing 901 to enable burst mode.

Next, the user may capture 903 a series of infrared (IR) images for averaging using the user interface 116 and trigger control 112 to command the processor 222 to capture a plurality of frames. These frames are preferably taken consecutively, but in some embodiments they may not be. For example, in an embodiment, the camera may choose to discard a frame if it does not meet certain criteria. A visible light (VL) image of the scene may be additionally captured via the aforementioned visible light camera module 206. The camera, such as via its processor 222 running a programmed algorithm, then performs post processing steps 904, aligning and averaging the images. During the calculation process, the user may experience an hourglass or other icon or image on the display 108 indicating the camera is performing processing steps. A live thermal image may not be shown on display 108 during processing. In certain circumstances, this situation may be undesirable to the user. In other embodiments, a live thermal image may be available to view on display 108 during processing. During processing, the user may abort 997 the calculation, resulting in the return of live thermal imagery to the display 108 and readying the device for further use 998. If the calculation is not aborted, the camera will align and average the IR images, resulting 905 in an averaged thermal scene. In some embodiments, the averaged thermal scene may have a visible light image associated therewith. The processing steps of alignment and averaging of an embodiment of the invention are detailed further in FIG. 9*b*. After a camera has acquired 910 a series of n IR images, it selects 911 one of said images to be a reference image. In certain embodiments, the processor selects the first of the series of acquired images as the reference image. In other embodiments, other images from the series may be selected. The processor 222 next performs an alignment calculation 912 such as those mentioned above to determine how much, if any, the n−1 frames other than the reference frame are shifted from the reference frame. In other words, if there is an object within a scene that is substantially fixed, i.e. a non-moving object with respect to the camera, its pixel coordinates in each frame should match. However, they may not always do so due to instability of the object, camera, operator, or any other factor that may introduce unintended position changes of elements within the scene. Accordingly, the calculation for alignment is done to determine the degree of shift each of the n−1 non-reference frames must go through in order to be properly aligned with the reference frame. Although image correlation and other methods are noted above, any known method of determining spatial shifts between images may be employed.

Upon calculation 912, n−1 new versions of the non-reference images are created, each now being aligned with the reference image. These images are averaged together 913, via processor 222, for instance, to create 914 a final, temporally averaged IR image with a NETD reduced from the original image by a factor of $\sqrt{n}$ and, as discussed previously, may also include an associated VL image.

In some embodiments, the thermal imaging device may capture both infrared (IR) and visible light (VL) images. In further embodiments, these VL and IR images may be captured substantially simultaneously, wherein the pixel coordinates of elements within the scene will not have changed between the capturing of the VL and IR frames. In such an embodiment, the camera may use the VL images to perform the alignment of multiple frames prior to the averaging of the IR data. Since the IR and VL scenes were taken at least substantially simultaneously, any misalignment among IR scenes should be similarly manifested within the VL scenes. Accordingly, determining the misalignment among the VL scenes results in knowing the misalignment among the associated IR scenes, thereby allowing for them to be adequately aligned and averaged appropriately. Since VL images often provide better contrast between different objects than is provided by IR images, it is sometimes much easier to determine the spatial shifts between captured frames by analyzing (e.g., correlating or performing some other alignment calculation) the VL images rather than by analyzing the IR images for. This process of using both VL and IR images is detailed in FIG. 9*c*.

Figure 9B:
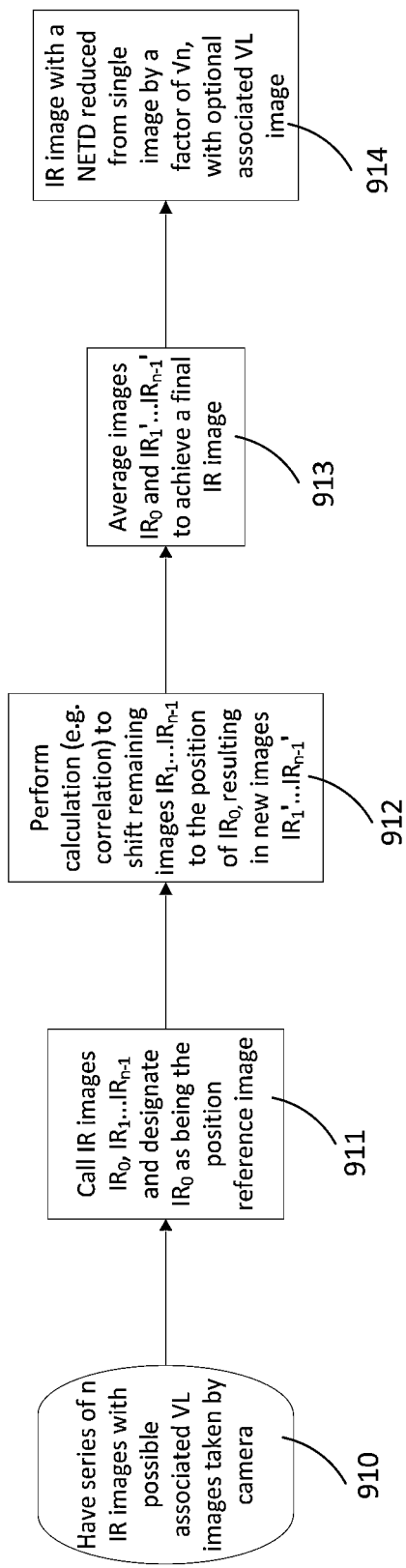
FIG. 9b is a process flow diagram detailing the post-processing of a series of infrared images.
Figure 9C:
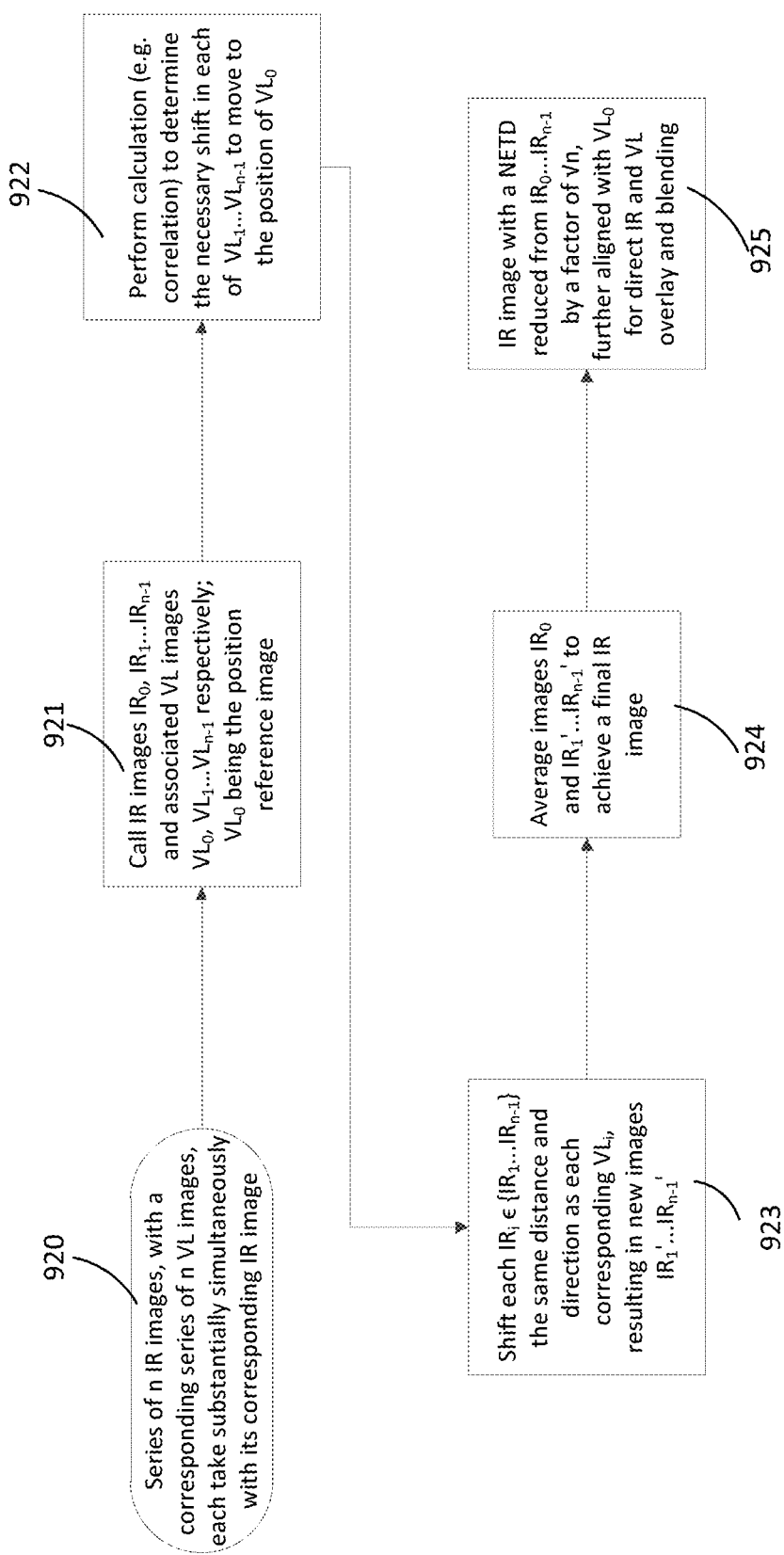
FIG. 9c is a process flow diagram detailing the post-processing of a series of infrared images using a corresponding series of visible light images.

In this embodiment, a camera captures 920 a series of n IR and n associated VL images, with each IR and its associated VL image being captured substantially simultaneously as one another. Next, one VL image is selected 921, by the processor 222 for instance, to be the reference image. Subsequently, a calculation 922 similar to the one discussed in the description of FIG. 9*b* is carried out, only this time calculating the offset in position of each of the n−1 non-reference VL images. Upon determining the deviation from the reference image for each of the additional n−1 VL images, each IR image is shifted 923 by its corresponding VL image misalignment amount. Since the IR and VL images were taken substantially simultaneously and the optics of each are fixed relative to each other, any offset in the VL images from the reference image will likely be equally present in the IR images. As such, performing this shift of IR images will act to align them just as it would align the VL images. Once aligned, the IR images are averaged 924 as described in the description of FIG. 9*b*, resulting 925 in an averaged IR image with a NETD reduced by a factor of $\sqrt{n}$ from a non-averaged IR image. This image has associated with it a VL image, namely the reference VL image used in the alignment step.

This embodiment may be preferable in the situation where there is low thermal contrast, such as the situation described above when a reduction in noise may greatly aid the quality of the image. This embodiment may be advantageous because elements helpful in defining position such as edges and corners may not be very abrupt or clear in the IR image of low contrast. It may be the case that, while the thermal contrast is low, these edges and corners are very clear and distinct within the VL image. If this is the case, the alignment calculation may be much more accurate or made much more easily while using the VL images as opposed to the IR images.

In other embodiments, IR and associated VL images need not be captured substantially simultaneously in order to perform the aforementioned process of aligning IR images by performing calculations on the VL images. Rather, using the VL images in order to align the IR images may be possible using factors such as frame capture times of and physical separation between the VL and IR camera modules. Using these or other known values, a reasonable IR image alignment may be calculated from VL images captured at substantially different times as the associated IR images.

Example thermal image cameras and related techniques have been described. The techniques described in this disclosure may also be embodied or encoded in a computer-readable medium, such as a non-transitory computer-readable storage medium containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), a hard disk, optical media, or other computer readable media.

Various examples have been described. These and other examples are within the scope of the following claims.

The invention claimed is:

1. A thermal imaging camera comprising:
   an infrared (IR) lens assembly having at least one associated IR sensor for detecting IR images of a target scene, the IR sensor comprising a plurality of pixels, each pixel having a unique coordinate location;
   a display adapted to display at least a portion of the IR images; and
   at least one processor programmed with instructions to
      capture a plurality of generally consecutive frames of IR images of a single target scene, wherein, among the frames, the pixel coordinate of a substantially fixed feature in the scene may differ,
      perform an alignment calculation by which the frames are generally adjusted relative to one another such that the substantially fixed feature from one of the frames has approximately the same pixel coordinate in each of the other frames, and
      average the adjusted frames to create an average IR image of the scene with improved quality.

2. The camera of claim 1, wherein the alignment calculation uses frames of IR images captured consecutively.

3. The camera of claim 1, wherein the number of the plurality of generally consecutive frames captured can be selected from a list of different options.

4. The camera of claim 3, wherein the list of different options further contains selection possibilities of "2", "4", or "8".

5. The camera of claim 1, wherein the alignment calculation consists of at least a correlation.

6. The camera of claim 1, where improving an image quality includes at least improving the thermal sensitivity.

7. The camera of claim 6, wherein improving the thermal sensitivity comprises effectively reducing the NETD of the camera and/or the IR images.

8. The method of claim 1 wherein an icon is displayed during processing.

9. The camera of claim 1, wherein the alignment calculation can be aborted by a user of the camera.

10. The camera of claim 1, further comprising a visible light (VL) lens assembly and having at least one associated VL sensor for detecting VL images of the target scene; the display being adapted to display at least a portion of the VL image and/or a portion of the IR image.

11. The camera of claim 10, wherein the alignment calculation is performed using a plurality of VL images, each corresponding to an associated IR image.

12. The method of claim 11 wherein the plurality of VL images are captured substantially simultaneously with the corresponding IR images.

13. The camera of claim 11, wherein the calculation uses images taken consecutively.

14. The camera of claim 10, wherein the number of the plurality of generally consecutive frames to be captured can be selected from a list of different options.

15. The camera of claim 14, wherein the list comprising a plurality of frame options further contains selection possibilities of "2", "4", or "8".

16. The camera of claim 10, wherein the alignment calculation includes a correlation.

17. The camera of claim 10, wherein improving an image quality includes improving the thermal sensitivity.

18. The camera of claim 17, wherein improving the thermal sensitivity comprises effectively reducing the NETD of the camera and/or image(s).

19. A method for producing a thermal image comprising:
   capturing a plurality of frames of infrared (IR) images of a single scene using a thermal imaging camera, the camera comprising at least one processor, some of the frames being captured from slightly different fields of view such that the scene is located in different portions of the frames of some of the captured plurality of IR images;
   performing an alignment calculation by the processor that adjusts the frames such that the scene in the captured plurality of IR images is aligned; and
   averaging the adjusted frames to create an averaged IR image of the scene with improved quality.

20. The method of claim 19, wherein the camera captures an additional, equal plurality of visible light (VL) images, each associated with a corresponding IR image.

21. The method of claim 20, wherein the alignment calculation is performed using the plurality of VL images.

22. The method of claim 21, wherein the VL images and the corresponding IR images are captured substantially simultaneously.

23. The method of claim 20, wherein the camera is a portable, hand-held thermal imaging camera.

* * * * *